United States Patent [19]

Andersson et al.

[11] Patent Number: 4,950,659
[45] Date of Patent: Aug. 21, 1990

[54] 16,17-ACETALSUBSTITUTED ANDROSTANE-17β-CARBOXYLIC ACID ESTERS PROSSESSING HIGH BINDING AFFINITY TO THE GLUCOCORTICOSTEROID RECEPTOR

[75] Inventors: Paul H. Andersson, Södra; Sandby; Per T. Andersson, Lund; Bengt I. Axelsson, Genarp; Bror A. Thalen, Bjaärred; Jan W. Trofast, Lund, all of Sweden

[73] Assignee: Aktiebolaget Draco, Lund, Sweden

[21] Appl. No.: 843,771

[22] Filed: Mar. 25, 1986

[30] Foreign Application Priority Data

Apr. 4, 1985 [SE] Sweden .................... 8501693

[51] Int. Cl.$^5$ .............. C07J 31/00; C07J 71/00; A61K 31/56; A61K 31/565
[52] U.S. Cl. .................. 514/172; 260/397.1; 260/397.45; 514/179; 540/61; 540/63
[58] Field of Search ............ 514/179, 172; 260/397.1, 397.45; 540/66, 61, 63

[56] References Cited

U.S. PATENT DOCUMENTS

3,828,080  8/1974  Phillipps et al. .......... 260/397.1
3,981,894  9/1976  Phillipps et al. .......... 260/397.1

FOREIGN PATENT DOCUMENTS

3126732  3/1982  Fed. Rep. of Germany ............ 260/397.45
3149475  7/1982  Fed. Rep. of Germany ............ 260/397.45
378109  11/1973  Sweden ............ 260/397.45
396079  1/1974  Sweden ............ 260/397.45
436572  8/1977  Sweden ............ 260/397.45

*Primary Examiner*—Floyd D. Higle
*Attorney, Agent, or Firm*—White & Case

[57] ABSTRACT

The invention refers to compounds having anti-inflamatory activity characterized by the formula

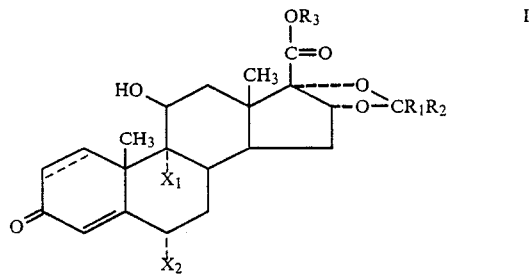

or a stereoisomeric component thereof, in which formula the 1,2-position is saturated or is a double bond
$X_1$ is selected from hydrogen, fluorine, chlorine and bromine
$X_2$ is selected from hydrogen, fluorine, chlorine and bromine
$R_1$ is selected from hydrogen or a straight or branched hydrocarbon chain having 1-4 carbon atoms
$R_2$ is selected from hydrogen or straight and branched hydrocarbon chains having 1-10 carbon atoms and
$R_3$ is selected from

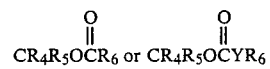

is O or S
$R_4$ is selected from hydrogen, straight or branched hydrocarbon chains having 1-10 carbon atoms or from phenyl
$R_5$ is selected from hydrogen or methyl and
$R_6$ is selected from hydrogen, straight or branched, saturated or unsaturated hydrocarbon chains having 1-10 carbon atoms, an alkyl group substituted by at least one halogen atom, a heterocyclic ring system containing 3-10 atoms in the ring system,

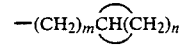

(m=0,1,2; n=2,3,4,5,6), phenyl or benzyl groups which are unsubstituted or substituted by one or more alkyl, nitro, carboxy, alkoxy, halogen, cyano, carbalkoxy or trifluoromethyl group(s), provided that when $R_2$ is hydrogen $R_1$ is methyl.

The invention also refers to a process and intermediates for the prearation of these compounds, a pharmaceutical preparation containing one of the compounds and a method for the treatment of inflammatory conditions.

9 Claims, No Drawings

16,17-ACETALSUBSTITUTED ANDROSTANE-17β-CARBOXYLIC ACID ESTERS PROSSESSING HIGH BINDING AFFINITY TO THE GLUCOCORTICOSTEROID RECEPTOR

DESCRIPTION

1. Field of the Invention

The present invention relates to novel, pharmacologically active compounds and to intermediates and a process for their use in mammals, including humans. The invention also relates to pharmaceutical compositions containing the compounds and to methods of treatment of inflammatory, allergic, muscoskeletal or dermatological conditions with these compounds.

The object of the invention is to provide a glucocorticosteroid which possesses high anti-inflammatory potency on the place of application and low glucocorticoid systemic potency.

2. Background Art

It is known that certain glucocorticosteroids (GCS) can be used for local therapy of inflammatory, allergic or immunologic diseases in respiratory airways (e.g. asthma, rhinitis), in skin (eczema, psoriasis) or in bowel (ulcerative colitis, Morbus Crohn). With such local glucocorticoid therapy, clinical advantages over general therapy (with e.g. glucocorticoid tablets) are obtained, expecially regarding reduction of the unwanted glucocorticoid effects outside the diseased area. To reach such clinical advantages, in e.g. severe respiratory airway disease, GCS must have a suitable pharmacological profile. They should have high intrinsic glucocorticoid activity at the application site but also a rapid inactivation by e.g. hydrolysis in the target organ or after uptake into the general circulation.

Since binding of GCS to the glucocorticoid receptor is a pre-requisite for their anti-inflammatory and allergic effects to occur, the ability of steroids to bind to their receptor(s) can be used as an adequate method for determining the biological activity of GCS. A direct correlation between the affinity of GCSs to the receptor and their antiinflammatory effects has been shown using ear edema test in the rat. [Correlation between chemical structure, receptor binding, and biological activity of some novel, highly active, 16α,17α-acetalsubstituted glucocorticoids. E. Dahlberg, A. Thalen, R. Brattsand, J-A Gustafsson, U. Johansson, K. Roempke, and T. Saartok, Mol. Pharmacol. 25 (1984), 70.]

DISCLOSURE OF THE INVENTION

The present invention is based on the observation that certain 3-oxo-androsta-1,4-diene-17β-carboxylic acid esters possess high binding affinity to the glucocorticosteroid receptor. The compounds of the invention can be used for the treatment and control of inflammatory conditions.

The compounds of the invention are characterized by the formula

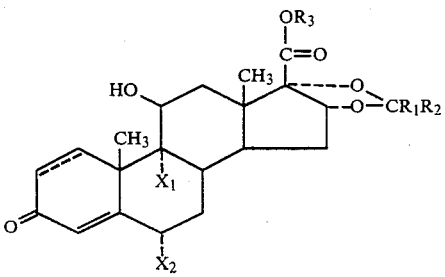

wherein
the 1,2-position is saturated or is a double bond
$X_1$ is selected from hydrogen, fluorine, chlorine and bromine
$X_2$ is selected from hydrogen, fluorine, chlorine and bromine
$R_1$ is selected from hydrogen or a straight or branched hydrocarbon chain having 1–4 carbon atoms
$R_2$ is selected from hydrogen or straight and branched hydrocarbon chains having 1–10 carbon atoms and
$R_3$ is selected from

Y is O or S
$R_4$ is selected from hydrogen, straight or branched hydrocarbon chains having 1–10 carbon atoms or from phenyl
$R_5$ is selected from hydrogen or methyl and
$R_6$ is selected from hydrogen, straight or branched, saturated or unsaturated hydrocarbon chains having 1–10 carbon atoms, an alkyl group substituted by at least one halogen atom, a heterocyclic ring system containing 3–10 atoms in the ring system, $-(CH_2)_mCH(CH_2)_n$ (m=0,1,2; n=2,3,4,5,6), phenyl or benzyl groups which are unsubstituted or substituted by one or more alkyl, nitro, carboxy, alkoxy, halogen, cyano, carbalkoxy or trifluoromethyl group(s), provided that when $R_2$ is hydrogen $R_1$ is methyl.

The individual stereoisomeric components present in a mixture of a steroid having the above formula (I) can be elucidated in the following way:

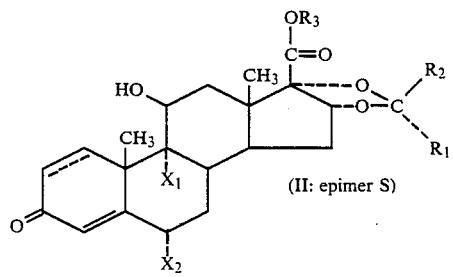

(II: epimer S)

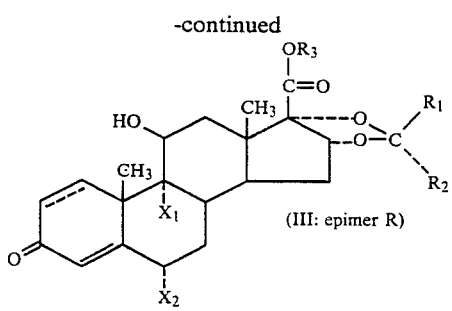

The individual stereoisomeric components present, in a mixture of steroid 17β-carboxylic acid esters having the formulas

or

where St is the steroid moiety, can be elucidated in the following way

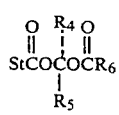

and

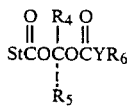

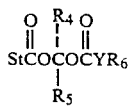

In diasteroisomers like II, III, VI, VII, VIII and IX, the configuration differs only at one out of several asymmetric carbon atoms. Such diastereoisomers are denoted epimers.

Alkyl in the definitions above is a straight or branched hydrocarbon chain with 1–5 carbon atoms, preferably 1–4 C.

Alkoxy in the definition above is a group —O—alkyl wherein the alkyl moiety has the above given definition.

Halogen in the definition above is preferably a chlorine, bromine or fluorine atom.

Carbalkoxy in the definition above is a group —COO— alkyl wherein the alkyl moiety has the above given definition.

Heterocyclic ring system is a ring system containing as hetero atoms N, O or S.

Preferred systems are pyrryl, pyrridyl, pyrimidyl, pyrazinyl, furyl, pyranyl, benzofuranyl, indolyl and thienyl.

Particular compounds of the invention which are preferred:

1'-Ethoxycarbonyloxyethyl 6α,9α-difluoro-11β-hydroxy-16α,17α-[(1-methylethylidene)bis(oxy)]-androsta-1,4-diene-3-one-17β-carboxylate, the epimeric mixture A+B and epimer B.

1'-isopropoxycarbonyloxyethyl 9α-fluoro-11β-hydroxy-15α,17α-[(1-methylethylidene)bis(oxy)]-androsta-1,4-diene-3-one-17β-carboxylate, epimer B.

1'-proposycarbonyloxyethyl 6α,9α-difluoro-11β-hydroxy-16α,17α-[(1-methylethylidene)bis(oxy)]androxta-1,4-diene-3-one-17α-carboxylate, epimer B.

1'-isopropoxycarbonyloxyethyl 6α,9α-difluoro-11β-hydroxy-16α,17α-[(1-methylethylidene)bis(oxy)]androsta-1,4-diene-3-one-17β-carboxylate, epimeric mixture A+B and epimer B.

1'-Acetoxyethyl (20R)-9α-fluoro-11β-hydroxy-16α,17α-propylmethylenedioxyandrosta-1,4-diene-3-one-17β-carboxylate, epimer B.

1'-Ethoxycarbonyloxyethyl (22R)-9α-fluoro-11β-hydroxy-16α,17α-propylmethylenedioxyandrosta-1,4-diene-3-one-17β-carboxylate, epimer B.

1'-isopropoxycarbonyloxyethyl (20R)-9α-fluoro-11β-hydroxy-16α,17α-propylmethylenedioxyandrosta-1,4-diene-3-one-17β-carboxylate, epimer B.

1'-Ethoxycarbonyloxyethyl (20R)-6α,9α-difluoro-11β-hydroxy-16α,17α-propylmethylenedioxyandrosta-1,4-diene-3-one-17β-carboxylate, epimeric mixture A+B and epimer B.

METHODS OF PREPARATION

The compounds of the invention are prepared by the oxidation of a compound of the formulas X, XI and XII to the corresponding 17β-carboxylic acid:

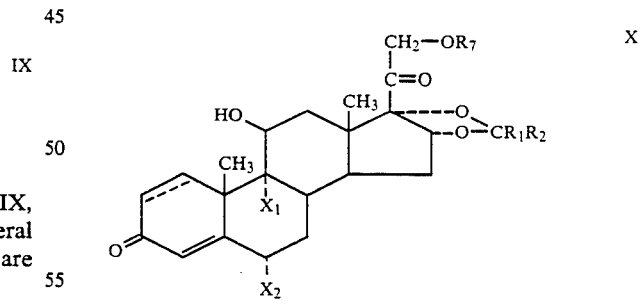

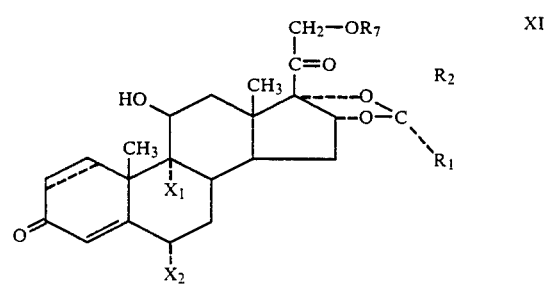

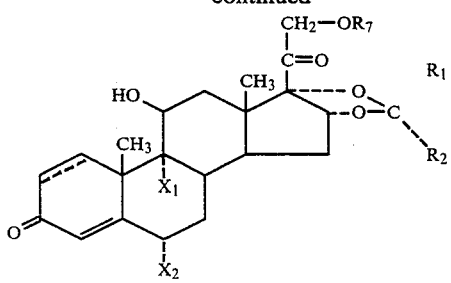

wherein the solid and broken lines between C-1 and C-2 represent a single or double bond, $X_1$, $X_2$, $R_1$ and $R_2$ have the meaning given above, and $R_7$ is hydrogen or an acyl group with 1-10 carbon atoms arranged in a straight or branched chain, The 17β-carboxylic acids then are esterified to give compounds characterized by the formula I-IX, wherein $\equiv\equiv\equiv$ $X_1$, $X_2$, $R_1$, $R_2$ and $R_3$ have the meaning given above.

The process of this invention to convert a compound of formulas X, XI or XII to the corresponding 17-carboxylic acids is carried out in a suitable oxygenated hydrocarbon solvent such as a lower alkanol. Methanol and ethenol are preferred, particularly the former. The reaction medium is made slightly alkaline by the addition of a suitable weak inorganic base such as an alkali metal carbonate, for example sodium, lithium or potassium carbonate. The latter is preferred. The conversion of a compound of formula X, XI or XII to a 17β-carboxylic acid of formula I, II, or III ($R_3=H$) takes place at ambient temperatures, i.e. 20°-25° C.

The presence of oxygen is necessary for the reaction. Oxygen can be supplied by bubbling a stream of air or oxygen into the reaction mixture.

The oxidative degradation of the 17β side-chain of compounds of formula X, XI and XII to the corresponding 17β carboxylic acids can also be carried out with periodic acid, sodium hypobromate or with sodium bismuthate. The reaction is performed in a mixture of water and a suitable oxygenated hydrocarbon solvent such as a lower ether. Dioxane and tetrahydrofurane are preferred, particularly the former.

The parent 17β-carboxylic acids of compounds of formula I, II and III ($R_3=H$) may be esterified in known manner to provide 17β carboxylate esters according to the invention. For example, the 17β-carboxylic acid may be reacted with an appropriate alcohol and a carbodiimide, e.g. dicylohexylcarbodiimide, in a suitable solvent such as diethylether, tetrahydrofurane, methylene chloride or pyridine advantageously at a temperature of 25°-100° C. Alternatively, a salt of the 17β-carboxylic acid with an alkali metal, e.g. lithium, sodium or potassium, a salt of a quaternary ammonium compound, such as a salt or triethyl- or tributylamine, or tetrabutylammonium, may be reacted with an appropriate alkylating agent, for example an acyloxyalkylhalide or haloalkyl alkylcarbonate preferably in a polar solvent medium such as acetone, methylethylketone, or dimethyl formamide, dimethyl sulphoxide, mthylenechloride or chloroform, conveniently at a temperature in the range 25°-100° C. The reaction may also be performed in the presence of a crown ether.

The crude steroid ester derivatives formed are after isolation purified by chromatography on a suitable material, for instance cross-linked dextran gels of Sephadex ® LH-type with suitable solvents as eluants, e.g. halogenated hydrocarbons, ethers, esters such as ethyl acetate or acetonitrile.

The individual epimers, which are formed at the acetalisation of the 16α,17α-hydroxy groups or at the esterification of the 17β-carboxylic acids, possess practically identical solubility characteristics. Accordingly, they have turned out to be impossible to separate and isolate from the epimeric mixture by conventional method for resolution of stereoisomers, e.g. fractionated crystallization. In order to obtain the individual epimers separately the stereoisomeric mixtures according to the formulas I, IV and V above are subjected to column chromatography, thus separating the epimers II, III, VI, VII, VIII and IX in view of different mobility on the stationary phase. The chromatography may be carried out for instance on cross-linked dextran gels of the type Sephadex ® LH, e.g. Sephadex ® LH-20 in combination with a suitable organic solvent as eluting agent. Sephadex ® LH-20, prepared by Pharmacia Fine Chemicals AB, Uppsala, Sweden, is a beadformed hydroxyproylated dextran gel wherein the dextran chains are cross-linked to give a three-dimensional polysaccharide network. As eluting agent, halogenated hydrocarbons e.g. chloroform or a mixture of heptane-chloroform-ethanol in the proportions 0–50:50–100:-10–1 has successfully been used, preferably a 20:20:1 mixture.

As starting materials for the compounds of the invention compounds of the formulas X, XI and XII are used. They are prepared by reaction of compounds with the formula

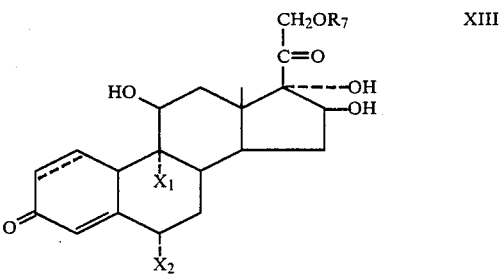

wherein the solid and broken lines between C-1 and C-2 represent a single or double bond, and $X_1$, $X_2$ and $R_7$ have the meaning given above, with an aldehyde of the formula

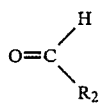

wherein $R_2$ has the meaning given above.

The aldehyde is preferably acetaldehyde, propanal, butanal, isobutanal, pentanal, 3-methylbutanal, 2,2-dimethylpropanal, hexanal, heptanal, octanal, nonanal, and dodecanal. The reaction is carried out by adding the steroid to a solution of the aldehyde together with an acid catalyst, e.g. perchloric acid, p-toluene sulphonic acid, hydrochloric acid in an ether, preferably dioxane, or halogenated hydrocarbons, preferably methylene chloride or chloroform.

Compounds X, XI and XII are also prepared by transacetalisation of the corresponding 16α,17α-acetonides

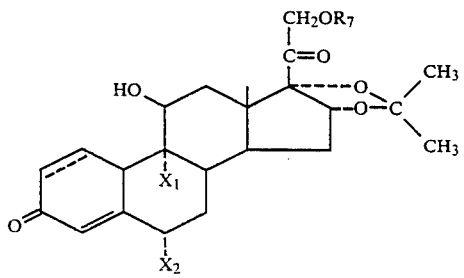

wherein the solid and broken lines between $C_1$ and $C_2$ represent a single or double bond and $X_1$, $X_2$ and $R_7$ have the meaning given above with an aldehyde of the formula

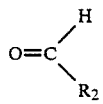

wherein $R_2$ has the meaning given above.

The aldehyde is preferably acetaldehyde, propanal, butanal, isobutanal, pentanal, 3-methylbutanal, 2,2-dimethylpropanal, hexanal, heptanal, octanal, nonanal and dodecanal. The reaction is carried out by adding the steroid to a solution of the aldehyde together with a strong inorganic acid as catalyst, preferably perchloric or hydrochloric acid, in an ether, preferably dioxane or tetrahydrofurane, a halogenated hydrocarbon, preferably methylene chloride or chloroform, an aromatic hydrocarbon, preferably toluene, an alicyclic hydrocarbon, preferably cyclohexane or an aliphatic hydrocarbon, preferably heptane or isooctane, under the latter conditions eliminating the chromatographic step for preparation of the epimers III and XII.

PHARMACEUTICAL PREPARATIONS

The compounds of the invention may be used for different modes of local administration dependent on the site of inflammation, e.g. percutaneously, parenterally or for local administration in the respiratory tract by inhalation. An important aim of the formulation design is to reach optimal bioavailability of the active steroid ingredient. For percutaneous formulations this is advantageously achieved if the steroid is dissolved with a high thermodynamic activity in the vehicle. This is attained by using a suitable system of solvents comprising suitable glycols, such as propylene glycol or 1,3-butandiol either as such or in combination with water.

It is also possible to dissolve the steroid either completely or partially in a lipophilic phase with the aid of a surfactant as a solubilizer. The percutaneous compositions can be an ointment, an oil in water cream, a water in oil cream or a lotion. In the emulsion vehicles the system comprising the dissolved active component can make up the disperse phase as well as the continuous one. The steroid can also exist in the above compositions as a micronized, solid substance.

Pressurized aerosols for steroids are intended for oral or nasal inhalation. The aerosol system is designed in such a way that each delivered dose contains 10-1000 µg, preferably 20-250 µg of the active steroid. The most active steroids are administered in the lower part of the dose range. The micronized steroid consists of particles substantially smaller than 5 µm, which are suspended in a propellent mixture with the assistance of a dispersant, such as sorbitan trioleate, oleic acid, lecithin or sodium salt or dioctylsulphosuccinic acid.

WORKING EXAMPLES

The invention will be further illustrated by the following non-limitative examples. In the examples a flow-rate of 2.5 ml/cm$^2$.h$^{-1}$ is used at the preparative chromatographic runs. Molecular weights are in all examples determined with electron impact mass spectrometry and the melting points on a Leitz Wetzlar hot stage microscope. All HPLC analyses (HPLC=High Performance Liquid Chromatography) were performed on a Waters µBondapak $C_{18}$ column (300×3.9 mm internal diameter) with a flow-rate of 1.0 ml/min and with ethanol-water in ratios between 50:50 and 60:40 as mobile phase, if not otherwise stated.

EXAMPLE 1

This example sets forth a process for preparing (22RS)-, (22R)- and (b 22S)-11β,16α,17α,21-tetrahydroxypregna-1,4-diene-3,20-dione 16α,17α-acetals.

Preparation of (22RS)-, (22R)- and (22S)-16α,17α-butylidenedioxy-6α,9α-difluoro-11β,21-dihydroxy-pregna-1,4-diene-3,20-dione.

A. To a suspension of 1.0 g of 6α,9α-difluoro-11β,16α,17α,21-tetra-hydroxypregna-1-4-diene-3,20-dione in 500 ml of methylene chloride 0.32 ml of freshly distilled n-butanal and 2 ml of 72% perchloric acid were added. The reaction mixture was allowed to stand for 24 h at room temperature under stirring. The reaction mixture was washed with 10% aqueous potassium carbonate solution and water, dried over sodium sulphate and evaporated. The residue was dissolved in ethyl acetate and precipitated with petroleum ether leaving 883 mg of (22RS)-16α,17α-butylidenedioxy-6α,9α-difluoro-11β,21-dihydroxypregna-1,4-diene-3,20-dione. HPLC-analysis showed 99% purity and the ratio 16:84 between the 22S- and 22R-epimers. Molecular weight: 466 (calculated 466.5). The (22RS) epimeric mixture was chromatographed on Sephadex LH-20 column (76×6.3 cm) using heptane:chloroform:ethanol, 20:20:1, as mobile phase. The fractions 12315–13425 ml (A) and 13740–15690 ml (B) were collected and evaporated and the residue dissolved in methylene chloride and precipitated with petr.-ether. Fraction A gave 62 mg of (22S)- and fraction B 687 mg of (22R)-16α,17α-butylidenedioxy-6α,9α-difluoro-11α,21-dihydroxypregna-1,4-diene-3,20-dione. The (22S)-epimer: Molecular weight 466 (calculated 466.5), m.p. 196≧-200° C. The (22R)-epimer: Molecular weight 466 (calculated 466.5), m.p. 169°-72° C.

B. To a solution of 1.0 g of 6α,9α-difluoro-11β,21-dihydroxy-16α,17α-[(1-methylethylidene)bis(oxy)]-pregna-1,4-diene-3,20-dione in 500 ml of methylene chloride was added 0.30 ml freshly distilled n-butanal and 2 ml of 72% perchloric acid. The reaction mixture was allowed to stand for 24 h at 33+ C. under stirring, extracted with aqueous potassium carbonate and water, dried over sodium sulphate and evaporated. The residue was dissolved in methylene chloride and precipitated with petr.-ether yielding 848 mg of (22RS)-16α,1-7α-butylidenedioxy-6α,9α-difluoro-11β,21-dihydroxypregna-1,4-diene-3,20-dione. HPLC-analysis showed purity and the ratio 12/88 between the 22S- and 22R-epimers.

B'. To a suspension of 4.0 g of 6α,9α-difluoro-11β,21-dihydroxy-16α,17α-[(methylethylidene)bis(oxy)]pregna-1,4-diene-3,20-dione in 100 ml of heptane was added 1.2 ml of freshly distilled n-butanal and 3.8 ml of perchloric acid (72%). The reaction mixture was allowed to stand for 5 h at room temperature under vigorous stirring, extracted with aqueous potassium carbonate and water, dried over sodium sulphate and evaporated yielding 4.0 g of (22RS)-16α,17α-butylidenedioxy-6α,9α-difluoro-11β,21-dihydroxypregna-1,4-diene-3,20-dione. HPLC-analysis showed 98.5% purity and the ratio 3/97 between the 22S- and 22R-epimers. After two recrystalisations from chloroform-petroleum ether 3.1 g of 22R-epimer was obtained, which contained only 1.1% of the 22S-epimer and 1.3% of other impurities.

C. Similarly, by following the procedure set forth in the example by substituting 6α,9α-difluoro-11β,16α,17α,21-tetrahydroxypregna-1,4-diene-3,20-dione for 11β,16α,17α,21-tetrahydroxypregna-1,4-diene-3,20-dione, 9α-fluoro- and 6α-fluoro-11β,16α,17α,21-tetrahydroxypregna-1,4-diene-3,20-dione or the corresponding 16α,17α-acetonides non-fluorinated and fluorinated non-symmetric (22RS)-, (22R)- and (22S)-11β,16α,17α,21-tetrahydroxypregna-1,4-diene-3,20-dione 16α,17α-acetals from acetaldehyde, propanal, butanal, isobutanal, pentanal, 3-methylbutanal, 2,2-dimethylpropanal, hexanal, heptanal, octanal, nonanal, and dodecanal are prepared.

EXAMPLE 2

A. Prednacinolon 16α,17α-acetonide (250 mg; 0,5 mmol) was dissolved in 75 ml of CH$_2$Cl$_2$. n-Butanal (130 mg; 1,8 mmol and 70% perchloric acid (0,025 ml) were added. The solution was stirred at 33° C. for 15 hours. The yellow solution was washed with 2×10 ml of 10% K$_2$CO$_3$ and 4×10 ml of H$_2$O, dried and evaporated. Yield: 257 mg (97,7%). HPLC gave 91,1% purity. Unreacted acetonide consists of 7,4% of the impurities. Epimer ratio 14,6/85,4.

B. Trimcinolon 16α,17α-acetonide (0,5 g; 1,1 mmol) was dissolved in 150 ml of CH$_2$Cl$_2$. n-Butanal (260 mg; 3,6 mmol) and 70% perchloric acid (0,22 ml) were added. The mixture way stirred at 33° C. for 16 hours. CH$_2$Cl$_2$ was taken over into a separation funnel and the reaction flask was washed several times with 10 ml K$_2$CO$_3$ and CH$_2$Cl$_2$, respectively. The solution was then washed with 2×10 ml of 10% K$_2$CO$_3$ and 4×10 ml of H$_2$O, dried and evaporated. Yield: 438 mg (84,9%). HPLC gave 80,2% purity. Epimer ratio 19/81.

C. Fluocinolon 16α,17α-acetonide (0,5 g; 1,1 mmol) was dissolved in 150 ml of CH$_2$Cl$_2$. n-Butanal (260 mg; 3,6mmol) and 70% perchloric acid (0,22 ml) were added. The mixture was stirred at 33° C. for 24 hours. The CH$_2$Cl$_2$ phase was taken over into a separation funnel. The reacton flask was washed several times with 15 ml of 10% K$_2$CO$_3$ and CH$_2$Cl$_2$, respectively. The solution was washed with 2×15 ml of 10% K$_2$CO$_3$ and 4×15 ml of H$_2$O, dried and evaporated. Yield: 513 mg (100%). HPLC gave 97,4% purity. Epimeric ratio 8.6/91,4.

EXAMPLE 3

This example sets forth a process for preparing 11β-hydroxy-16α,17α-[(1-methylethylidene)bis(oxy)]- and (20RS)-, (20R)- and (20S)-11β-hydroxy-16α,17α-alkylmethylenedioxyandrosta-1,4-diene-3-one-17β-carboxylic and -4-ene-3-one-17β-carboxylic acids.

Preparation of 6α,9α-difluoro-11β-hydroxy-16α,17α-[(1-methylethylidene)-bis(oxy)]androsta-1,4-diene-3-one-17β-carboxylic acid.

A. To a solution of 1.99 g of fluocinolone 16α,17α-acetonide in 120 ml of methanol 40 ml of 20% aqueous potassium carbonate was added. A stream of air was bubbled though this solution for about 20 h under stirring at room temperature. The methanol was evaporated and 200 ml of water was added to the residue. The solution was extracted with methylene chloride. The aqueous phase was acidified with diluted hydrochloric acid. The precipitate formed was collected by filtration and dried to yield 1.34 g of 6α,9α-difluoro-11β-hydroxy-16α,17α-[(1-methylethylidene)-bis(oxy)androsta-1,4-diene-3-one-17β-carboxylic acid, melting point 264°-68° C., molecular weight 438. The purity determined by HPLC was 94.0%. The aqueous phase was extracted with ethyl acetate. After drying the solvent was evaporated leaving another 0.26 g portion of acid. Purity: 93.7%.

B. Periodic acid (15.1 g) in 16.5 ml of water was added to a solution of fluocinolone 16α,17α-acetonide (5.0 g) in 55 ml dioxane. The reaction mixture was stirred at room temperature for 20 h, neutralized with saturated aqueous sodium hydrogen carbonate and evaporated. The residue was dissolved in 200 ml of methylene chloride and washed with 8×100 ml 10% aqueous potassium carbonate. The aqueous phase was acidified with conc. hydrochloric acid and extracted with 6×100 ml of ethyl acetate. After drying the solvent was evaporated. The residue was dissolved in 400 ml of ethyl acetate and precipitated with petroleum ether yielding 3.69 g of 6α,9α-difluoro-11β-hydroxy-16α,17α-[(1-methylethylidene)bis(oxy)androsta-1,4-diene-3-one-17β-carboxylic acid. The purity determined by HPLC was 99.5%.

C. Similarly, by following the procedure set forth in the example by substituting fluocinolone 16α,17α-acetonide for 11β,16α,17α,21-tetrahydroxypregna-1,4-diene-3,20-dione, 6α-fluoro-11β,16α,17α,21-tetrahydroxypregna-1,4-diene-3,20-dione, and triamcinolone 16α,17α-acetonide 11β-hydroxy-16α,17α-[(1-methylethylidene)bis(oxy)]androsta-1,4-diene-3-one-17β-carboxylic acids are prepared. By substituting the 16α,17α-acetonide group for 16α,17α-acetals between 16α-hydroxyprednisolone 6α-fluor-16α-hydroxyprednisolone, triamcinolone and fluocinolone and acetaldehyde, propanal, butanal, isobutanal, pentanal, 3-methylbutanal, 2,2-dimethylpropanal, hexanal, heptanal, octanal, nonanal and dodecanal and their 21-esters (20RS)-(20R)- and (20R)-11β-hydroxy-16α,17α-alkylmethylenedioxyandrosta-1,4-diene- and 4-ene-3-one-17β-carboxylic acids are prepared.

EXAMPLE 4

1'-Ethoxycarbonyloxyethyl 6α,9α-difluoro-11β-hydroxy-16α,17α-[(1-methylethylidene)bis(oxy)]androsta-1,4-diene-3-one-17β-carboxylate.

A. 6α,9α-Difluoro-11β-hydroxy-16α,17α-[(1-methylethlidene)bis(oxy)]-androsta-1,4-diene-3-one-17β-carboxylic acid (600 mg) and potassium hydrogen carbonate (684 mg) were dissolved in 45 ml of dimethyl formamide. 1-Bromoethyl ethyl carbonate (2 ml) was added and the reaction mixture stirred at room temperature overnight. Water (200 ml) was added and the mixture was extracted with methylene chloride. The combined extracts were washed with 5% aqueous sodium hydrogen carbonate and water, and the residue purified by chromatography on a Sephadex LH-20 column (72×6.3 cm) using chloroform as mobil phase. The fraction 1515-2250 ml was collected and evaporated yielding 480 mg of 1'-ethoxycarbonyloxyethyl 6α,9α-difluoro-11β-hydroxy-16α,17α-[(1-methylethylidene)-bis(oxy)]-androsta-1,4-diene-3-one-17β-carboxylate. The purity determined by HPLC was 98.1% and the ratio epimer A/B, 48/52. Melting point: 218°-27° C. $[\alpha]_D^{25} = +63.2°$ (c=0.214; $CH_2Cl_2$). The molecular weight was 554.

The 1'-ethoxycarbonyloxyethyl 6α,9α-difluoro-[11β-hydroxy-16α,17α-(1-methylethylidene)bis(oxy)]androsta-1,4-diene-3-one-17β-carboxylate (480 mg) was chromatographed on a Sephadex LH-20 column (76×6.3 cm) using heptane:chloroform:ethanol, 20:20:1, as mobile phase. The fraction 2325-2715 ml was collected, evaporated and the residue dissolved in methylene chloride and precipitated by petroleum ether giving 200 mg of a compound (A) of purity 97.3% (determined by HPLC analysis). Melting point: 246°-50° C. $[\alpha]_D^{25} = +100.5°$ (c=0.214; $CH_2Cl_2$). The molecular weight was 554.

The fraction 4140-5100 ml yielded 250 mg of a compound (B) with purity 99.0%. Melting point: 250°-55° C. $[\alpha]_D^{25} = +28.5°$ (c=0.246; $CH_2Cl_2$). The molecular weight was 554. The methine signal from the ester group is shifted 0.13 ppm downfield in $^1$H-NMR spectrum of B compared to A, while the rest of the spectra are nearly identical. The electron impact mass spectra of A and B are identical apart from the intensities of the mass peaks. These spectroscopic differences and similarities indicate that A and B are epimers due to the chiral center in the ester group.

B. 6α,9α-Difluoro-11β-hydroxy-16α,17α-[(1-methylethylidene)bis)oxy)]androsta-1,4-diene-3-one-17β-carboxylic acid (200 mg) was dissolved in 25 ml of dimethylformamide. 1-Chloroethyl ethyl carbonate (100 mg), potassium hydrogen carbonate (70 mg) and 18-crown-6-ether were added. The reaction mixture was stirred at 80° C. for 3 g, cooled, extracted with methylene chloride after addition of 150 ml of water, dried ad evaporated. The crude product was purified in the same way as in procedure A leaving 207 mg of 1'-ethoxycarbonyloxyethyl 6α,9α-difluoro-11β-hydroxy-16α,17α- [(1-methylethylidene)bis(oxy)]androsta-1,4-diene-3-one-17β-carboxylate. The purity (HPLC) was 98.4% and the ratio epimer A/B, 54/46.

C. 6α,9α-Difluoro-11β-hydroxy-16α,17α-[(1-methylethylidene)bis(oxy)]androsta-1,4-diene-3-one-17β-carboxylic acid (200 mg) and 1,5-diazabicyclo [5.4.0] undecene-5 (140 mg) were suspended in 25 ml of benzene and warmed to reflux. A solution of 1-bromo-ethyl ethyl carbonate (175 mg) in 5 ml of benzene was added and the mixture was refluxed for 2 ½ h. After cooling 50 ml of methylene chloride was added and the solution was washed with water, dried and evaporated. The crude product was purified in the same way as in procedure A, yielding 207 mg of 1'-ethoxycarbonyloxyethyl 6α,9α-difluoro-11β-hydroxy-16α,17α-[(1-methylmethylethylidene)bis(oxy)]androsta-1,4-diene-3-one-17β-carboxylate. The purity (HPLC) was 96.4% and the ratio epimer A/B, 44/56.

D. To a solution of 6α,9α-difluoro-11β-hydroxy-16α,17α-[(1-methylethylidene)bis(oxy)]androsta-1,4-diene-3-one-17β-carboxylic acid (100 mg) in 25 ml of acetone 175 mg of α-bromodiethylcarbonate and 45 mg of anhydrous potassium carbonate were added. The mixture was heated for 6 h at reflux. The cooled reaction mixture was poured into 150 ml of water and extracted with methylene chloride. The extract was washed with water, dried over sodium sulphate and evaporated yielding 65 mg of solid 1'-ethoxycarbonyloxyethyl 6α,9α-difluoro-11β-hydroxy-16α,17α, [(1-methyolethylidene)bis(oxy)] androsta-1,4-diene-3-one-17β-carboxylate. The purity determined by HPLC was 97.6% and the ration epimer A/B, 49/51.

E. 6α,9αDifluoro-11β-hydroxy-16α,17α-[(1-methylethylidene)bis(oxy)] androsta-1,4-diene-3-one-17β-carboxylic acid (500 mg) and tetrabutylammonium hydrogen sulphate (577 mg) were added to 3 ml of 1M sodium hydroxide. A solution of 435 mg of 1-bromethyl ethyl carbonate in 50 ml of methylene chloride was added. The mixture was refluxed with stirring overnight. The two layers were separated. The organic layer was washed with 2×10 ml of water, dried and evaporated. The crude product was purified by chromatography on a Sephadex LH-20 column (72×6.3 cm) using chloroform as mobile phase. The fraction 1545-1950 ml was collected and evaporated and the residue precipitated from methylene chloride—petroleum ether leaving 341 gm of 1'-ethoxycarbonyloxyethyl 6α,9α-difluoro-11β-hydroxy-16α,17α- [(1-methylethylidene)-bis(oxy)]androsta-1,4-diene-3-one-17β-carboxylate. The purity determined with HPLC was 99.2% and the ratio epimer A/B, 56/44.

F. 6α,9α-Difluoro-11β-hydroxy-16α,17α-[(1-methylethylidene)bis-(oxy)]androsta-1,4-diene-3-one-17β-carboxylic acid (200 mg) and tricaprylmethylammonium chloride (200 mg) were added to 5 ml of saturated aqueous $NaHCO_3$. A solution of 100 mg of 1-bromoethyl ethyl carbonate in 10 ml of methylene chloride was added. The mixture was stirred at 45° C. for 20 h, diluted with 10 ml of methylene chloride and isolated and purified in the same way as in procedure E yielding 254 mg of 1'-ethoxycarbonyloxyethyl 6 α,9α-difluoro-11β-hydroxy-16α,17α-[(1-methylethylidene)bis(oxy)]-androsta-1,4-diene-3-one-17β-carboxylate. The purity (HPLC) was 97.4% and the ratio epimer A/B, 60/40.

G. 6α,9α-Difluoro-11β-hydroxy-16α,17α-[(1-methylethylidene)bis(oxy)]androsta-1,4-diene-3-one-17β-carboxylic acid (200 mg), 1-bromoethyl ethyl carbonate (135 mg) and triethylamine (275 mg) were dissolved in 20 ml of dimethylformamide. The mixture was stirred at 80° C. for 3 h, diluted with 200 ml of methylene chloride, washed with water, dried and evaporated. The crude product was purified in the same way as in procedure A yielding 69 mg of 1'-ethoxycarbonyloxyethyl 6α,9α-difluoro-11β-hydroxy-16α,17α- [(1-methylethylidene)bis(oxy)]androsta-1,4-diene-3-one-17β-carboxylate. The purity (HPLC) was 97.8% and the ratio epimer A/B, 48/52.

EXAMPLE 5

1'-Acetoxyethyl 6α,9α-difluoro-11β-hydroxy-16α,17α-[(1-methylethylidene)bis(oxy)]androsta-1,4-diene-3-one-17β-carboxylate.

6α,9α-Difluoro-11β-hydroxy-16α,17α-[(1-methylethylidene)bis(oxy)]androsta-1,4-diene-3-diene-3-one- 17β-carboxylic acid (500 mg) and potassium hydrogen carbonate (575 mg) were dissolved in 40 ml of dimethylformamide. 1-chloroethyl acetate (1 ml) was added and the reaction mixture was stirred at room temperature for 40 h. The reaction mixture was poured into 50 ml of water and extracted with methylene chloride. The extract was washed with aqueous sodium hydrogen carbonate and water, dried and evaporated. The residue was chromatographed on Sephadex LH-20 column (72×6.3 cm) using chloroform as mobile phase. The fractions 1755–2025 and 2026–2325 ml were collected and evaporated.

The solid product from fraction 1755–2025 ml was further purified by chromatography on a sephadex LH-20 column (76×6.3 cm i.d.) using a mixture of heptane-chloroform-ethanol, 20:20:1, as mobile phase. The fraction 2505–2880 ml was collected and evaporated. the residue was dissolved in methylene chloride and precipitated with petroleum ether leaving 167 mg of solid product (A). The purity determind by HPLC was 99.1%. Melting point 238°–59° C. $[\alpha]_D^{25} = +94°$ (C=0.192; $CH_2Cl_2$). The molecular weight was 524.

The solid product from fraction 2026–2325 ml above was further purified by chromatography in the same way as above. The fraction 5100–5670 ml was collected and evaporated. The residue was dissolved in methylene chloride and precipitated with petroleum ether yielding 165 mg of solid product (B). The purity determined with HPLC was 99.4%. Melting point 261°–65° C. $[\alpha]_D^{25} = +34°$ (c=0.262; $CH_2Cl_2$). The molecular weight was 524.

The $^1$H-NMR spectra of A and B are nearly identical with the exception of the methine quartet from the ester group which is shifted 0.16 ppm downfield in compound B compared to A. The fragmentation patterns of A and B in electron impact mass spectra are identical apart from the intensities of the mass peaks. These spectroscopic properties A and B indicate that they are epimers due to the chiral center in the ester group.

EXAMPLE 6~88

The substance given in Table 1-3 below were prepared, isolated and purified in a manner analogous to that described in Examples 4 and 5.

TABLE 1

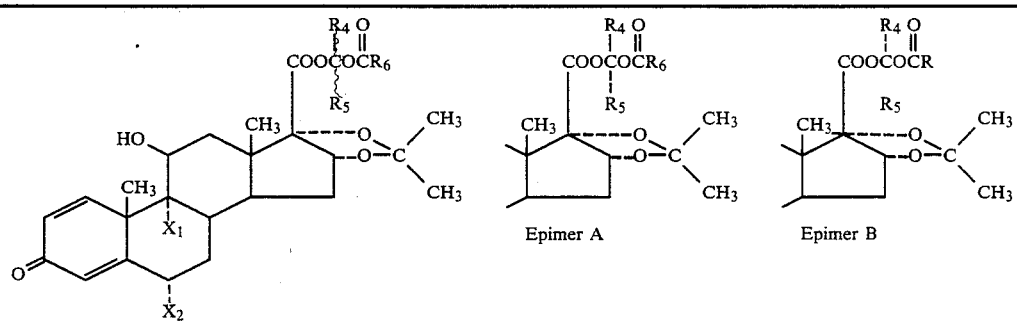

| Example no. | $X_1$ | $X_2$ | $R_4$ | $R_5$ | $R_6/YR_6$ | Epimer | Mp °C. | $[\alpha]_D^{25}$ (c = 0.2 in $CH_2Cl_2$) | Molecular weight calc. | found | Retention volume (ml) |
|---|---|---|---|---|---|---|---|---|---|---|---|
| 6 | H | H | fenyl | H | $CH_3$ | A | 242 (dec) | +79° | 550.7 | 550 | 1665–1890[1] |
| 7 | H | H | fenyl | H | $CH_3$ | B | 221 (dec) | +89° | 550.7 | 550 | 1891–2175[1] |
| 8 | F | H | $CH(CH_3)_2$ | H | $CH_3$ | A | — | +102° | 534.6 | 534 | 2325–2580[1] |
| 9 | F | H | $CH(CH_3)_2$ | H | $CH_3$ | B | — | +40° | 534.6 | 534 | 3165–3555[1] |
| 10 | F | H | fenyl | H | $CH_3$ | A | 249 (dec) | +73° | 568.6 | 568 | 2040–2355[1] |
| 11 | F | H | fenyl | H | $CH_3$ | B | 238 (dec) | +75° | 568.6 | 568 | 2895–3285[1] |
| 12 | F | F | $CH_3$ | H | $C(CH_3)_3$ | A | 262–70 | +87° | 566.6 | 566 | 2190–2505[1] |
| 13 | F | F | $CH_3$ | H | $C(CH_3)_3$ | B | 268–77 | +50° | 566.6 | 566 | 3525–3990[1] |
| 14 | F | F | $CH_3$ | H | fenyl | A | 224–30 | +96° | 586.6 | 586 | 2325–2625[1] |
| 15 | F | F | $CH_3$ | H | fenyl | B | 259–67 | +48° | 586.6 | 586 | 4350–4875[1] |
| 16 | F | F | $CH_3$ | $CH_3$ | $CH_3$ | — | 130–42 | +61° | 538.6 | 538 | 1965–2220[1] |
| 17 | F | H | $CH_3$ | H | $OC(CH_3)_3$ | A | 184–87 | +98° | 564.7 | 564 | 235–280[3] |
| 18 | F | H | $CH_3$ | H | $OC(CH_3)_3$ | B | >300 | +30° | 564.7 | 564 | 525–630[2] |
| 19 | H | F | $CH_3$ | H | $OCH(CH_3)_2$ | A | 250–53 | +109° | 550.6 | 550 | 1530–1770[1] |
| 20 | H | F | $CH_3$ | H | $OCH(CH_3)_2$ | B | 230–35 | +58° | 550.6 | 550 | 2295–2850[1] |
| 21 | F | F | $CH_3$ | H | $OCH_3$ | A | 235–42 | +102° | 540.6 | 540 | 590–690[2] |
| 22 | F | F | $CH_3$ | H | $OCH_3$ | B | 225–33 | +31° | 540.6 | 540 | 395–430[3] |
| 23 | F | F | $CH_3$ | H | $O(CH_2)_2CH_3$ | A | 224–31 | +106° | 568.6 | 568 | 410–495[2] |
| 24 | F | F | $CH_3$ | H | $O(CH_2)_2CH_3$ | B | 227–30 | +28° | 568.6 | 568 | 690–900[2] |
| 25 | F | F | $CH_3$ | H | $OCH(CH_3)_2$ | A + B | 205–28 | +59° | 568.6 | 568 | 1365–1560[5] |
| 26 | F | F | $CH_3$ | H | $OCH(CH_3)_2$ | A | 210–25 | +95° | 568.6 | 568 | 400–475[2] |
| 27 | F | F | $CH_3$ | H | $OCH(CH_3)_2$ | B | 242–47 | +31° | 568.6 | 568 | 625–780[2] |
| 28 | F | F | $CH_3$ | H | $OCH(CH_2CH_3)_2$ | A | 226–28 | +95° | 596.7 | 596 | 1785–2085[1] |
| 29 | F | F | $CH_3$ | H | $OCH(CH_2CH_3)_2$ | B | 183–97 | +30° | 596.7 | 596 | 3150–3600[1] |
| 30 | F | F | $CH_3$ | H | $OCH_2CH(CH_2CH_3)_2$ | A | 217–21 | +89° | 610.7 | 610 | 1725–1980[1] |
| 31 | F | F | $CH_3$ | H | $OCH_2CH(CH_2CH_3)_2$ | B | 207–10 | +30° | 610.7 | 610 | 3120–3480[1] |
| 32 | F | F | $CH_3$ | H | $OC(CH_3)_3$ | A + B | 170–78 | +65° | 582.6 | 582 | 1290–1920[5] |
| 33 | F | F | $CH_3$ | H | $OC(CH_3)_3$ | A | 177–79 | +100° | 582.6 | 582 | 255–310[3] |
| 34 | F | F | $CH_3$ | H | $OC(CH_3)_3$ | B | 190–92 | +27° | 582.6 | 582 | 650–800[2] |
| 35 | F | F | $CH_3$ | H | $OCH_2C(CH_3)_3$ | A + B | 208–36 | +60° | 596.7 | 596 | 1605–1995[1] |
| 36 | F | F | $CH_3$ | H | $OCH_2C(CH_3)_3$ | A | 248–56 | +98° | 596.7 | 596 | 1845–2130[1] |
| 37 | F | F | $CH_3$ | H | $OCH_2C(CH_3)_3$ | B | 226–28 | +28° | 596.7 | 596 | 3270–3750[1] |

TABLE 1-continued

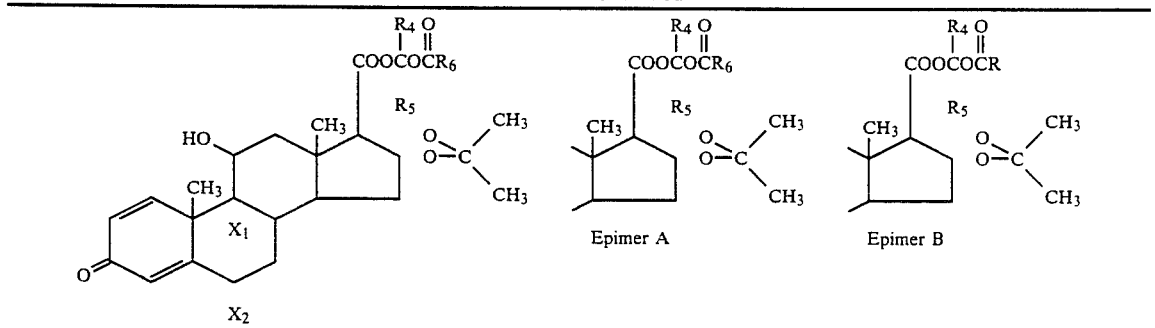

| Example no. | $X_1$ | $X_2$ | $R_4$ | $R_5$ | $R_6/YR_6$ | Epimer | Mp °C. | $[\alpha]_D^{25}$ (c = 0.2 in $CH_2Cl_2$) | Molecular weight calc. | found | Retention volume (ml) |
|---|---|---|---|---|---|---|---|---|---|---|---|
| 38 | F | F | $CH_3$ | $CH_3$ | $OCH_2CH_3$ | — | — | — | 568.6 | 568 | 405–460[2] |

[1] On a Sephadex LH-20 column (76 × 6.3 cm) using chloroform-heptane-ethanol (20:20:1) as mobile phase.
[2] On a Sephadex LH-20 column (87.5 × 2.5 cm) using chloroform-heptane-ethanol (20:20:1) as mobile phase.
[3] On a Sephadex LH-20 column (85 × 2.5 cm) using chloroform as mobile phase.
[4] On a Sephadex LH-20 column (72 × 6.3 cm) using chloroform as mobile phase.
[5] On a Sephadex LH-20 column (71.5 × 6.3 cm) using chloroform as mobile phase.

TABLE 2

| Example no. | $X_1$ | $X_2$ | $R_2$ | $R_4$ | $R_6/YR_6$ | Epimer | Mp °C. | $[\alpha]_D^{25}$ (c = 0.2 in $CH_2Cl_2$) | Molecular weight calc. | found | Retention volume (ml) |
|---|---|---|---|---|---|---|---|---|---|---|---|
| 39 | H | H | $CH_3$ | H | $C(CH_3)_3$ | — | 189–92 | +78° | 502.6 | 502 | 1290–1665[1] |
| 40 | H | H | $(CH_2)_2CH_3$ | H | $CH_3$ | — | 63–70 | +79° | 488.6 | 488 | 1110–1260[1] |
| 41 | H | H | $(CH_2)_2CH_3$ | H | $C(CH_3)_3$ | — | 192–96 | +74° | 530.7 | 530 | 1245–1440[1] |
| 42 | F | H | $(CH_2)_2CH_3$ | H | $C(CH_3)_3$ | — | 254–58 | +64° | 548.7 | 548 | 1485–1800[1] |
| 43 | H | H | $(CH_2)_2CH_3$ | H | $O(CH_2)_3CH_3$ | — | 40–46 | +70° | 546.7 | 546 | 1200–1395[1] |
| 44 | H | H | $(CH_2)_2CH_3$ | H | $OC(CH_3)_3$ | — | 155–58 | +67° | 546.7 | 546 | 320–400[2] |
| 45 | H | H | $(CH_2)_2CH_3$ | $CH_3$ | $OCH_2CH_3$ | A + B | 163–75 | +63° | 532.6 | 532 | 225–285[2] |
| 46 | F | H | $(CH_2)_2CH_3$ | $CH_3$ | $OCH_2CH_3$ | A + B | 138–60 | — | 550.6 | 550 | 1410–1545[1] |
| 47 | F | F | $(CH_2)_2CH_3$ | $CH_3$ | $OCH_2CH_3$ | A + B | 160–87 | — | 568.6 | 568 | 1620–2175[1] |

[1] On a Sephadex LH-20 column (72 × 6.3 cm) using chloroform as mobile phase.
[2] On a Sephadex LH-20 column (83 × 2.5 cm) using chloroform as mobile phase.

TABLE 3

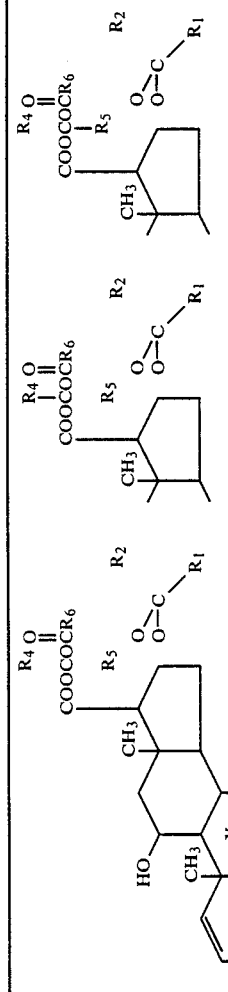

| Example no. | $X_1$ | $X_2$ | $R_1$ | $R_2$ | $R_4$ | $R_5$ | $R_6/YR_6$ | Epimer | Mp °C. | $[\alpha]_D^{25}$ (c = 0.2 in $CH_2Cl_2$) | Molecular weight calc. | Molecular weight found | Retention volume (ml) |
|---|---|---|---|---|---|---|---|---|---|---|---|---|---|
| 48 | H | H | $CH_3$ | H | H | H | $C(CH_3)_3$ | — | 192–97 | +67° | 502.6 | 502 | 1650–1995[1] |
| 49 | H | H | H | $CH_3$ | H | H | $C(CH_3)_3$ | — | 196–200 | +87° | 502.6 | 502 | 1305–1560[3] |
| 50 | H | H | $(CH_2)_2CH_3$ | H | H | H | $C(CH_3)_3$ | — | 261–67 | +69° | 548.7 | 548 | 1950–2100[1] |
| 51 | F | F | H | $(CH_2)_2CH_3$ | $CH_3$ | H | $C(CH_3)_3$ | — | 255–59 | +63° | 520.6 | 520 | 2145–2370[1] |
| 52 | F | H | $(CH_2)_2CH_3$ | H | $CH_3$ | H | $CH_3$ | A | 226–31 | +101° | 520.6 | 520 | 1905–2175[1] |
| 53 | F | H | $(CH_2)_2CH_3$ | H | $CH_3$ | H | $CH_3$ | B | 232–38 | +35° | 520.6 | 520 | 3300–3720[1] |
| 54 | F | H | H | $(CH_2)_2CH_3$ | $CH_3$ | H | $CH_3$ | A | 176–88 | +104° | 520.6 | 520 | 430–490[2] |
| 55 | F | H | H | $(CH_2)_2CH_3$ | $CH_3$ | H | $CH_3$ | B | 214–19 | +46° | 520.6 | 520 | 630–715[2] |
| 56 | F | H | H | $(CH_2)_2CH_3$ | $CH_3$ | H | $CH_3$ | A | 133–35 | +110° | 548.7 | 548 | 2100–2400[1] |
| 57 | F | H | H | $(CH_2)_2CH_3$ | $CH_3$ | H | $CH_3$ | B | 210–12 | +44° | 548.7 | 548 | 2850–3225[1] |
| 58 | F | H | H | $(CH_2)_2CH_3$ | $CH(CH_3)_2$ | H | $CH_3$ | A | 235–40 | +75° | 582.7 | 582 | 2100–2450[1] |
| 59 | F | H | H | $(CH_2)_2CH_3$ | $CH(CH_3)_2$ | H | $CH_3$ | B | 157–82 | +75° | 582.7 | 582 | 2760–3075[1] |
| 60 | F | H | H | H | fenyl | H | $CH_3$ | — | 140–42 | +77° | 546.7 | 546 | 1500–1665[1] |
| 61 | F | H | H | $(CH_2)_2CH_3$ | fenyl | H | $CH_3$ | — | 160–65 | +69° | 546.7 | 546 | 1620–1785[1] |
| 62 | F | H | $(CH_2)_2CH_3$ | H | H | H | $OC(CH_3)_3$ | — | 171–73 | +66° | 564.7 | 564 | 250–295[4] |
| 63 | F | H | H | $(CH_2)_2CH_3$ | H | H | $OC(CH_3)_3$ | — | 161–64 | +72° | 564.7 | 564 | 245–290[4] |
| 64 | F | H | H | $(CH_2)_2CH_3$ | H | H | $OCH_2CH_3$ | — | 203–11 | +99° | 554.6 | 554 | 325–370[4] |
| 65 | F | H | H | $(CH_2)_2CH_3$ | H | H | $OCH(CH_3)_2$ | A + B | 196–209 | +70° | 568.6 | 568 | 2235–2550[1] |
| 66 | F | H | H | H | $CH_3$ | H | $OCH_2CH_3$ | A + B | 138–52 | +102° | 532.6 | 532 | 300–370[2] |
| 67 | H | H | H | $(CH_2)_2CH_3$ | $CH_3$ | H | $OCH_2CH_3$ | A | 158–91 | +33° | 532.6 | 532 | 400–460[2] |
| 68 | F | H | H | $(CH_2)_2CH_3$ | $CH_3$ | H | $OCH_2CH_3$ | A | 196–98 | +110° | 550.7 | 550 | 405–475[2] |
| 69 | F | H | H | $(CH_2)_2CH_3$ | $CH_3$ | H | $OCH_2CH_3$ | B | 212–14 | +36° | 550.7 | 550 | 585–67[2] |
| 70 | F | H | H | $(CH_2)_2CH_3$ | $CH_3$ | H | $OC(CH_3)_3$ | A | 154–57 | +92° | 578.7 | 578 | 345–400[2] |
| 71 | F | H | H | $(CH_2)_2CH_3$ | $CH_3$ | H | $OC(CH_3)_3$ | B | 161–68 | +27° | 578.7 | 578 | 485–565[2] |
| 72 | F | H | H | $(CH_2)_2CH_3$ | $CH_3$ | H | $OCH(CH_3)_2$ | A | 221–24 | +107° | 564.7 | 564 | 355–425[2] |
| 73 | F | H | H | $(CH_2)_2CH_3$ | $CH_3$ | H | $OCH(CH_3)_2$ | B | 212–15 | +39° | 564.7 | 564 | 535–635[2] |
| 74 | F | H | H | $(CH_2)_2CH_3$ | $CH_3$ | H | $OC(CH_3)_3$ | A | 168–71 | +103° | 578.7 | 578 | 485–570[2] |
| 75 | F | H | H | $(CH_2)_2CH_3$ | $CH_3$ | H | $OC(CH_3)_3$ | B | 174–79 | +31° | 578.7 | 578 | 255–310[2] |
| 76 | F | H | $C(CH_3)_3$ | H | $CH_3$ | H | $OCH_2CH_3$ | A | 220–22 | +95° | 564.7 | 564 | 380–430 |
| 77 | F | H | $C(CH_3)_3$ | H | $CH_3$ | H | $OCH_2CH_3$ | B | 227–37 | +18° | 564.7 | 564 | 540–630[2] |
| 78 | F | H | H | $C(CH_3)_3$ | $CH_3$ | H | $OCH_2CH_3$ | A | 229–32 | +115° | 564.7 | 564 | 385–455[2] |
| 79 | F | H | H | $C(CH_3)_3$ | $CH_3$ | H | $OCH_2CH_3$ | B | 246–51 | +34° | 564.7 | 564 | 565–695[2] |
| 80 | F | F | $(CH_2)_2CH_3$ | H | $CH_3$ | H | $OCH_2CH_3$ | A | 167–70 | +95° | 568.6 | 568 | 300–330[5] |
| 81 | F | F | $(CH_2)_2CH_3$ | H | $CH_3$ | H | $OCH_2CH_3$ | B | 188–90 | +26° | 568.6 | 568 | 365–395[5] |

TABLE 3-continued

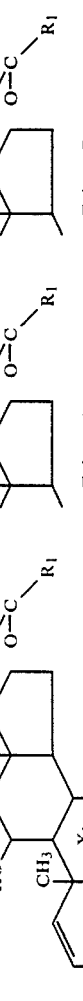

| Example no. | $X_1$ | $X_2$ | $R_1$ | $R_2$ | $R_4$ | $R_5$ | $R_6/YR_6$ | Epimer | Mp °C. | $[\alpha]_D^{25}$ (c = 0.2 in $CH_2Cl_2$) | Molecular weight calc. | Molecular weight found | Retention volume (ml) |
|---|---|---|---|---|---|---|---|---|---|---|---|---|---|
| 82 | F | F | H | $(CH_2)_2CH_3$ | $CH_3$ | H | $OCH_2CH_3$ | A + B | 178–96 | +68° | 568.6 | 568 | 3720–4155[1] |
| 83 | F | F | H | $(CH_2)_2CH_3$ | $CH_3$ | H | $OCH_2CH_3$ | A | 217–21 | +105° | 568.6 | 568 | 290–340[5] |
| 84 | F | F | H | $(CH_2)_2CH_3$ | $CH_3$ | H | $OCH_2CH_3$ | B | 211–15 | +32° | 568.6 | 568 | 341–395[5] |
| 85 | F | F | H | $(CH_2)_2CH_3$ | $CH_3$ | H | $OCH(CH_3)_2$ | A + B | 198–210 | +67° | 582.6 | 582 | 2190–3900[1] |
| 86 | F | F | H | $(CH_2)_2CH_3$ | $CH_3$ | H | $OCH(CH_3)_2$ | A | 232–37 | +96° | 582.6 | 582 | 2190–2355[1] |
| 87 | F | F | H | $(CH_2)_2CH_3$ | $CH_3$ | H | $OCH(CH_3)_2$ | B | 225–32 | +37° | 582.6 | 582 | 3630–3900[1] |
| 88 | F | F | H | $(CH_2)_2CH_3$ | $CH_3$ | $CH_3$ | $OCH_2CH_3$ | — | — | — | 582.6 | 582 | 385–440[2] |

[1]On a Sephadex LH-20 column (76 × 6.3 cm) using heptane-chloroform-ethanol (20:20:1) as mobile phase
[2]On a Sephadex LH-20 column (87.5 × 2.5 cm) using heptane-chloroform-ethanol (20:20:1) as mobile phase
[3]On a Sephadex LH-20 column (72 × 6.3 cm) using chloroform as mobile phase
[4]On a Sephadex LH-20 column (80 × 2.5 cm) using chloroform as mobile phase
[5]On a Sephadex LH-20 column (81.5 × 2.5 cm) using chloroform as mobile phase

EXAMPLE 89

Pharmaceutical Preparations

The following non-limitative examples illustrate formulations intended for different topical forms of administration. The amount of active steroid in the percutaneous formulations are ordinarily 0.001–0.2% (w/w), preferably 0.01–0.1% (w/w).

| Formulation 1, Ointment | | |
| --- | --- | --- |
| Steroid, micronized | 0.025 | g |
| Liquid paraffin | 10.0 | g |
| White soft paraffin | ad 100.0 | g |
| Formulation 2, Ointment | | |
| Steroid | 0.025 | g |
| Propylene glycol | 5.0 | g |
| Sorbitan sesquioleate | 5.0 | g |
| Liquid paraffin | 10.0 | g |
| White soft paraffin | ad 100.0 | g |
| Formulation 3, Oil in water cream | | |
| Steroid | 0.025 | g |
| Cetanol | 5.0 | g |
| Glyceryl monostearate | 5.0 | g |
| Liquid paraffin | 10.0 | g |
| Cetomacrogol 1000 | 2.0 | g |
| Citric acid | 0.1 | g |
| Sodium citrate | 0.2 | g |
| Propylene glycol | 35.0 | g |
| Water | ad 100.0 | g |
| Formulation 4, Oil in water cream | | |
| Steroid, micronized | 0.025 | g |
| White soft paraffin | 15.0 | g |
| Liquid paraffin | 5.0 | g |
| Cetanol | 5.0 | g |
| Sorbimacrogol stearate | 2.0 | g |
| Sorbitan monostearate | 0.5 | g |
| Sorbic acid | 0.2 | g |
| Citric acid | 0.1 | g |
| Sodium citrate | 0.2 | g |
| Water | ad 100.0 | g |
| Formulation 5, Water in oil cream | | |
| Steroid | 0.025 | g |
| White soft paraffin | 35.0 | g |
| Liquid paraffin | 5.0 | g |
| Sorbitan sesquioleate | 5.0 | g |
| Sorbic acid | 0.2 | g |
| Citric acid | 0.1 | g |
| Sodium citrate | 0.2 | g |
| Water | ad 100.0 | g |
| Formulation 6, Lotion | | |
| Steroid | 0.25 | mg |
| Isopropanol | 0.5 | ml |
| Carboxyvinylpolymer | 3 | mg |
| NaOH | q.s. | |
| Water | ad 1.0 | g |
| Formulation 7, Suspension for injection | | |
| Steroid, micronized | 0.05–10 | mg |
| Sodium carboxymethylcellulose | 7 | mg |
| NaCl | 7 | mg |
| Polyoxyethylene (20) sorbitan monoleate | 0.5 | mg |
| Phenyl carbinol | 8 | mg |
| Water, sterile | ad 1.0 | ml |
| Formulation 8, Aerosol for oral and nasal inhalation | | |
| Steroid, micronized | 0.1% | w/w |
| Sorbitan trioleate | 0.7% | w/w |
| Trichlorofluoromethane | 24.8% | w/w |
| Dichlorotetrafluoromethane | 24.8% | w/w |
| Dichlorodifluoromethane | 49.6% | w/w |
| Formulation 9, Solution for atomization | | |
| Steroid | 7.0 | mg |
| Propylene glycol | 5.0 | g |
| Water | ad 10.0 | g |
| Formulation 10, Powder for inhalation | | |
| A gelatin capsule is filled with a mixture of | | |
| Steroid, micronized | 0.1 | mg |
| Lactose | 20 | mg |

The powder is inhaled by means of an inhalation device.

PHARMACOLOGY

The affinity of the new androstane-17β-carboxylic acid esters to the glucocorticoid receptor All steroids according to the present invention are physiologically active compounds. The affinity of the novel androstane-17β-carboxylic acid esters to the glucocorticoid receptor has been used as a model for determination of the anti-inflammatory potency. Their receptor affinities have been compared to budesonide ([22R,S]-16α,17α-butylidenedioxy-11β,21-dihydroxy-pregna-1,4-diene-3,20-dione) a highly active glucocorticoid with a favourable ratio between local and systemic effects (Thalen and Brattsand, Arzneim.-Forsch. 29, 1687–90 (1979)).

Male Sprague-Dawley rats, one to two months of age, were used throughout the investigation. The thymus was removed and put into ice-cold saline. The tissue was homogenized in a Potter Elvehjem homogenizer in 10 ml of a buffer containing 20 mM Tris, pH 7.4, 10% (w/v) glycerol, 1 mM EDTA, 20 mM $NaMoO_4$, 10 mM mercaptoethanol. The homogenate was centrifuged for 15 min at $20,000 \times g$. Portions of the $20,000 \times g$ supernatant (230 μl) were incubated for about 24 h at 0° C. with 100 μl phenylmethylsulphonylfluoride (an esterase inhibitor, final conc. 0.5 mM). 20 μl unlabelled competitor and 50 μl $^3$H-labelled dexamethasone (final conc. 3 mM). Bound and free steroid were separated by incubating the mixture with 60 μl 2.5% (w/v) charcoal and 0.25% (w/v) dextran T70 suspension in 20 mM Tris, pH 7.4, 1 mM EDTA, and 20 mM $NaMoO_4$ for 10 min at 0° C. Following a centrifugation at $500 \times g$ for 10 min, 230 μl or the supernatant was counted in 10 ml Insta-Gel in a Packard scintillation spectrophotometer. The supernatants were incubated with (a) [$^3$H]dexamethasone alone, (b) [$^3$H]dexamethasone plus 1000 fold excess of unlabelled dexamethasone and (c) [$^3$H]dexamethasone plus 0.03–300 fold "excess" of competitor. The nonspecific binding was determined when 1000 fold excess of unlabelled dexamethasone was added to [$^3$H]-labelled dexamethasone.

The radioactivity bound to the receptor in the presence of competitor divided by the radioactivity bound to the receptor in the absence of competitor multiplied by 100 gives the percentage specific binding of labelled dexamethasone. For each concentration of a competitor the percentage specifically bound radioactivity is plotted against the log of concentration of competitor. The curves are compared at the 50% specific binding level and referenced to budesonide, which is assigned a relative binding affinity (RBA) of 1.

TABLE 4

Table summarizing relative binding affinities (RBA) to the glucocorticoid receptor of some of the investigated compounds.

| Compound according to Ex. No. | RBA |
| --- | --- |
| Budesonide | 1 |
| 4 epimer B | 0.30 |
| 5 epimer B | 0.17 |
| 27 | 0.50 |
| 38 | 0.04 |
| 55 | 0.20 |
| 64 | 0.05 |
| 67 | 0.04 |

TABLE 4-continued

Table summarizing relative binding affinities (RBA) to the glucocorticoid receptor of some of the investigated compounds.

| Compound according to Ex. No. | RBA |
|---|---|
| 69 | 0.44 |
| 84 | 1.03 |
| 87 | 0.63 |

We claim:

1. A compound of the formula

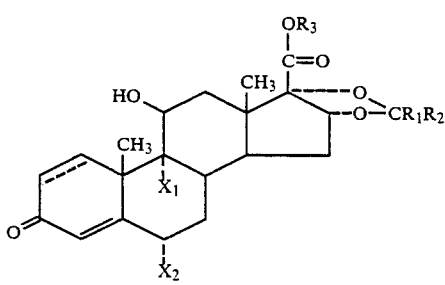

I of a stereoisomeric compound thereof, in which formula
the 1,2-position is saturated or is a double bond
$X_1$ is selected from hydrogen, fluorine, chlorine and bromine
$X_2$ is selected from hydrogen, fluorine, chlorine and bromine
$R_1$ is selected from hydrogen or a straight or branched hydrocarbon chain having 1-4 carbon atoms
$R_2$ is selected from hydrogen or straight and branched hydrocarbon chains having 1-10 carbon atoms and
$R_3$ is selected from

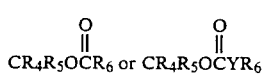

Y is O or S
$R_4$ is selected from hydrogen, straight or branched hydrocarbon chains having 1-10 carbon atoms or from phenyl
$R_5$ is selected from hydrogen or methyl and
$R_6$ is selected from hydrogen, straight or branched, saturated or unsaturated hydrocarbon chains having 1-10 carbon atoms, an alkyl group substituted by at least one halogen atom, a heterocyclic ring system containing 3-10 atoms in the ring system,

(m=0,1,2; n=2,3,4,5,6), phenyl or benzyl groups which are unsubstituted or substituted by one or more alkyl, nitro, carboxy, alkoxy, halogen, cyano, carbalkoxy or trifluoromethyl group(s),
provided that when $R_2$ is hydrogen $R_1$ is a straight or branched hydrocarbon chain having 1-4 carbon atoms.

2. A compound according to claim 1;
1'-Ethoxycarbonyloxyethyl 6α,9α-difluoro-11β-hydroxy-16α,17α-[(1-methylethylidene)bis(oxy)]-androsta-1,4-diene-3-one-17β-carboxylate,
1'-isopropoxycarbonyloxyethyl 9α-fluoro-11β-hydroxy-16α,17α-[(1-methylethylidene)bis(oxy)]-androsta-1,4-diene-3-one-17β-carboxylate,
1'-propoxycarbonyloxyethyl 6α,9α-difluoro-11β-hydroxy-16α,17α-[(1-methylethylidene)bis(oxy)]androsta-1,4-diene-3-one-17β-carboxylate,
1'-isopropoxycarbonyloxyethyl 6α,9α-difluoro-11β-hydroxy-16α,17α-[(1-methyyethylidene)bis(oxy)]androsta-1,4-diene-3-one-17β-carboxylate,
1'-Acetoxyethyl (20R)-9α-fluoro-11β-hydroxy-16α,17α-propylmethylenedioxyandrosta-1,4-diene-3-one-17β-carboxylate,
1'-Ethoxycarbonyloxyethyl (22R)-9α-fluoro-11β-hydroxy-16α,17α-propylmethylenedioxyandrosta-1,4-diene-3-one-17β-carboxylate,
1'-isopropoxycarbonyloxyethyl (20R)-9α-fluoro-11β-hydroxy-16α,17α-propylmethylenedioxyandrosta-1,4-diene-3-one-17β-carboxylate,
1'-Ethoxycarbonyloxyethyl (20R)-6α,9α-difluoro-11β-hydroxy-16α,17α-p-propylmethylenedioxyandrosta-1,4-diene-3-one-17β-carboxylate.

3. A pharmaceutical preparation comprising as active ingredient a compound according to claim 1.

4. A pharmaceutical preparation according to claim 3 in dosage unit form.

5. A pharmaceutical preparation according to claims 3 and 4 comprising the active ingredient in association with a pharmaceutically acceptable carrier.

6. A method for the treatment and control of inflammatory conditions in mammals characterized by the administration to a mammal in need of such treatment of an effective amount of a compound according to claim 1.

7. A compound according to claim 1 for use as an anti-inflammatory drug.

8. A compound of the formula

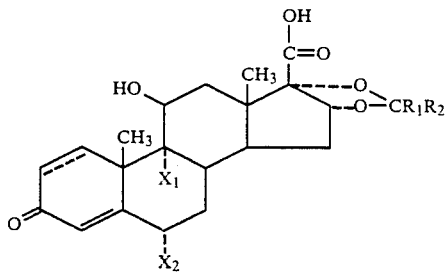

or a steroisomeric compound thereof, in which formula
the 1,2-position is saturated or is a double bond
$X_1$ is selected from hydrogen, fluorine, chlorine and bromine
$X_2$ is selected from hydrogen, fluorine, chlorine and bromine
$R_1$ is selected from hydrogen or a straight or branched hydrocarbon chain having 1-4 carbon atoms
$R_2$ is selected from hydrogen or straight and branched hydrocarbon chains having 1-10 carbon atoms,
providing that when $R_2$ is hydrogen $R_1$ is methyl.

9. A compound of the formula (26S)-1'-ethoxycarbonyloxyethyl (20R)-6α,9α-difluoro-11β-hydroxy-16α,17α-propylmethylenedioxyandrosta-1,4-dione-3-one-17β-carboxylate.

* * * * *

UNITED STATES PATENT AND TRADEMARK OFFICE
CERTIFICATE OF CORRECTION

Page 1 of 15

PATENT NO. : 4,950,659
DATED : August 21, 1990
INVENTOR(S) : Paul H. Andersson, et al.

It is certified that error appears in the above-identified patent and that said Letters Patent is hereby corrected as shown below:

Cover page, item [54] 3rd line of title, "PROSSESSING" should read --POSSESSING--;

Cover page, item [56] "Floyd D. Higle" should read --Floyd D. Higel--;

Cover page, item [57] Abstract, right col., first line under 1st chemical formula, "is O or S" should read --Y is O or S--;

Cover page, item [57] Abstract, right col., 3rd line from bottom, "prearation" should read --preparation--;

Cover page, item [57] Abstract, right col., 2nd & 3rd lines from bottom, "compund" should read --compound--;

Col. 1, line 5 (title), "PROSSESSING" should read --POSSESSING--;

Col. 1, line 34, "expecially" should read --especially--;

Col. 4, line 13, "-15$\alpha$, 17$\alpha$-" should read ---16$\alpha$,17$\alpha$---;

Col. 4, line 15, "1'- proposycarbon" should read --1'-propoxycarbon--;

Col. 4, line 17, "-17$\alpha$-" should read ---17$\beta$---;

Col. 5, line 18, "chain," should read --chain.--;

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

Col. 6, lines 21-22, "hydroxy-proylated" should read --hydroxypropylated--;

Col. 5, line 50, "dicylohexyl-carbodiimide" should read --dicyclohexylcarbodiimide--;

Col. 5, lines 61-62, "mthylene-chloride" should read --methylenechloride--;

Col. 8, line 10 "salt or" should read --salt of--;

Col. 8, line 28, "(b 22S)" should read --(22S)--;

Col. 8, line 55, "11α,21" should read --11β,21--;

Col. 8, line 65, "33 + C" should read --33°C--;

Col. 9, lines 3-4, "showed purity" should read --showed 93% purity--;

Col. 9, line 19, "recrystalisations" should read --recrystallizations--;

Col. 9, line 38, "(250 mg; 0,5 mmol)" should read --(250 mg; 0.6 mmol)--;

Col. 9, line 47, "Trimcinolon" should read --Triamcinolone--;

Col. 10, line 21, "-bis(oxy) androsta-" should read --bis(oxy)]androsta---;

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

Col. 10, line 40, "3.69g" should read --3.96g--;

Col. 10, line 41, "bis(oxy) androsta-" should read --bis(oxy)]androsta---;Col. 10, line 58, "and (20R)-" should read --and (20S)---;

Col. 10, line 67, "methyl-ethlidene" should read --methylethylidene--;

Col. 11, lines 18-19, "[11β-hydroxy-16α,17α-(1-methylethylidene)bis(oxy)]" should read --11β-hydroxy-16α,17α-[(1-methylethylidene)bis(oxy)]--;

Col. 11, line 48, "3g" should read --3h--;

Col. 11, line 50, "ad" should read --and--;

Col. 12, line 14, "[(1-methyolethylidene) should read --[(1-methylethylidene)--;

Col. 12, line 16, "ration" should read --ratio--;

Col. 12, line 17, "6α,9αDifluoro-" should read --6α,9α-Difluoro---;

Col. 12, line 21, "1-bromethyl" should read --1-bromoethyl--;

Col. 12, line 31, "341 gm" should read --341 mg--;

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

Col. 12, line 68, "-3-diene-3-one-" should read ---3-one---;

Col. 13, line 22, "C=0.192;" should read --c=0.192;--;

Col. 14, line 16, "properties A and B" should read --properties of A and B--;

Cols. 17 and 18, Table 3, right hand col., Retention Volume (ml), Example 58, "2100-2450$^1$" should read --2100-2400$^1$--;

Cols. 17 and 18, Table 3, right hand col., Retention Volume (ml), Example 69, "585-67$^2$" should read --585-670$^2$--;

Cols. 17 and 18, Table 3, right hand col., Retention Volume (ml), Example 76, "380-430" should read --380-430$^2$--;

Col. 23, line 25, "of" should read --or--;

Col. 24, line 8 "(1-methyyl-ethylidene) should read --(1-methylethylidene)--;

Col. 24, line 63 "4-dione-" should read --4-diene---;

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

```
col. 4, line 60, Compound XI, see attached;
col. 5, line 5, Compound XII, see attached;
col. 6, line 38, Compound XIII, see attached;
col. 14, Table 1, Epimer B, see attached;
col. 15 and col. 16, Table 1 (con't), see attached;
col. 15 and col. 16, Table 2, see attached;
col. 17 and col. 18, Table 3, see attached;
col. 19 and col. 20, Table 3 (con't), see attached;
col. 23, line 54, see attached;
col. 7, lines 25-29, see attached;
```

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

Col. 4, line 60, compound XI

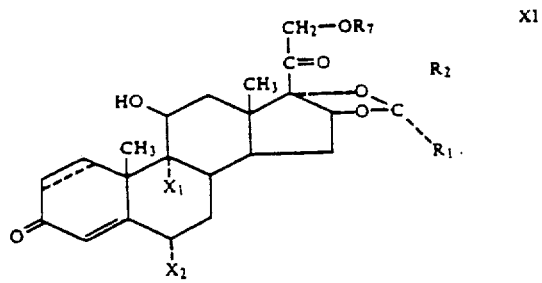

should read --

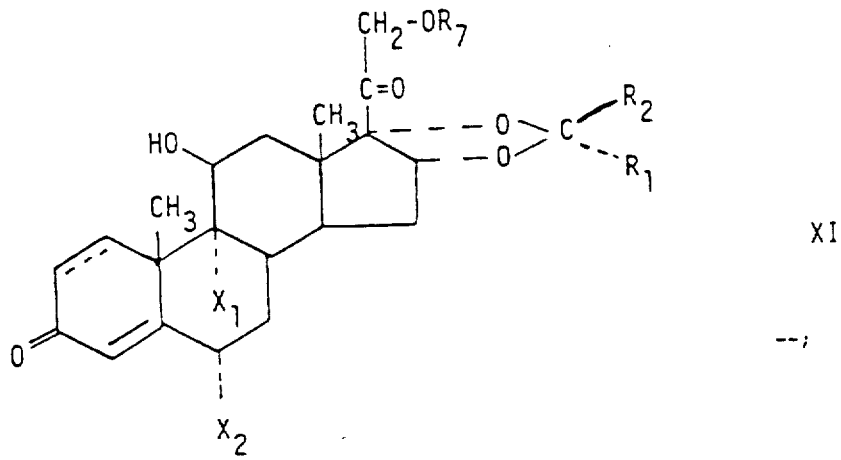

--;

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

Col. 5, line 5, compound XII,

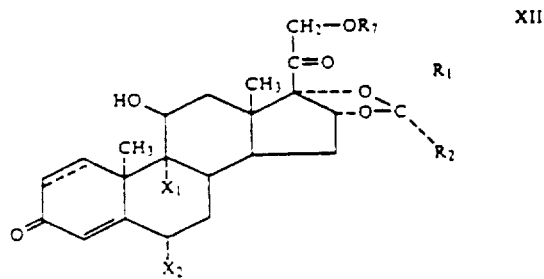

should read --

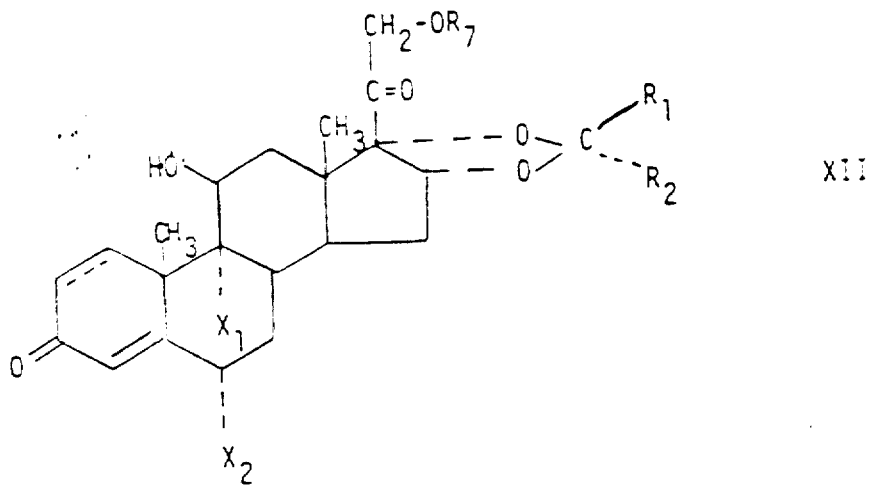

--;

UNITED STATES PATENT AND TRADEMARK OFFICE
CERTIFICATE OF CORRECTION

PATENT NO. : 4,950,659
DATED : August 21, 1990
INVENTOR(S) : Paul H. Andersson, et al.

It is certified that error appears in the above-identified patent and that said Letters Patent is hereby corrected as shown below:

col. 6, line 38, compound XIII,

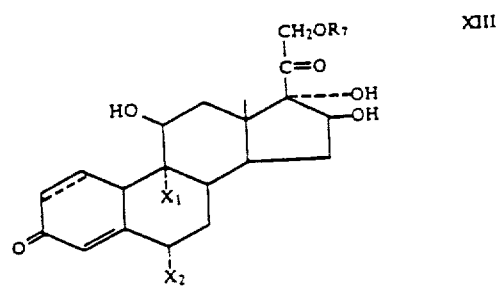

should read --

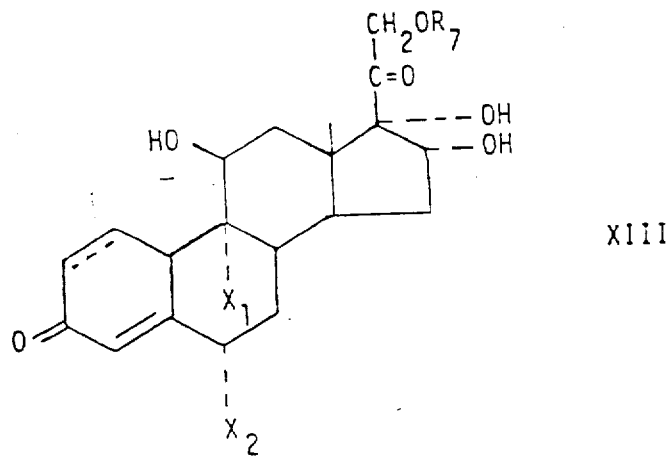

--;

UNITED STATES PATENT AND TRADEMARK OFFICE
CERTIFICATE OF CORRECTION

PATENT NO. : 4,950,659                    Page 9 of 15
DATED     : August 21, 1990
INVENTOR(S) : Paul H. Andersson, et al.

It is certified that error appears in the above-identified patent and that said Letters Patent is hereby corrected as shown below:

Col. 7, lines 25-29

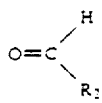

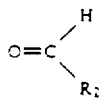

should read --

--;

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

Col. 14, Table 1, Epimer B,

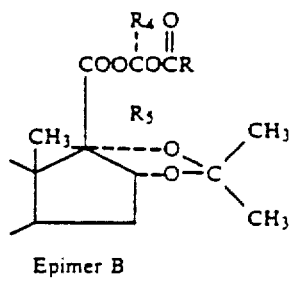

Epimer B should read --

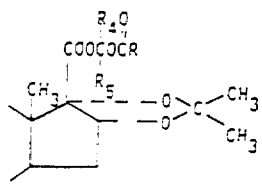

Epimer B

--;

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

Col. 15 and Col. 16 Table 1 (cont'd)

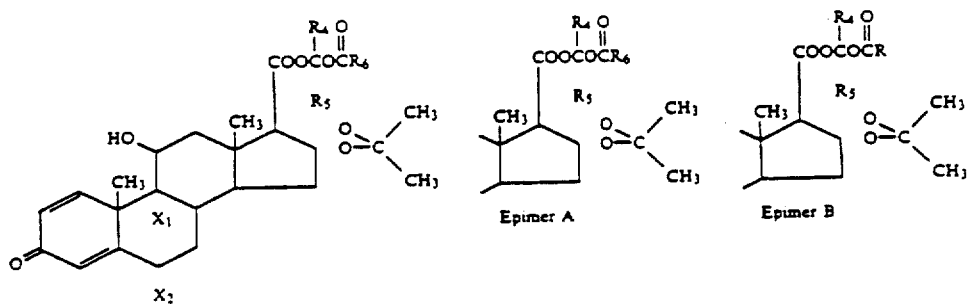

should read --

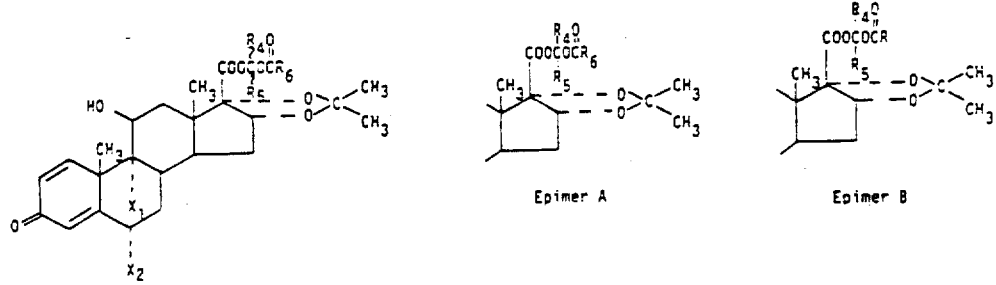

--;

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

Col. 15 and Col. 16, Table 2,

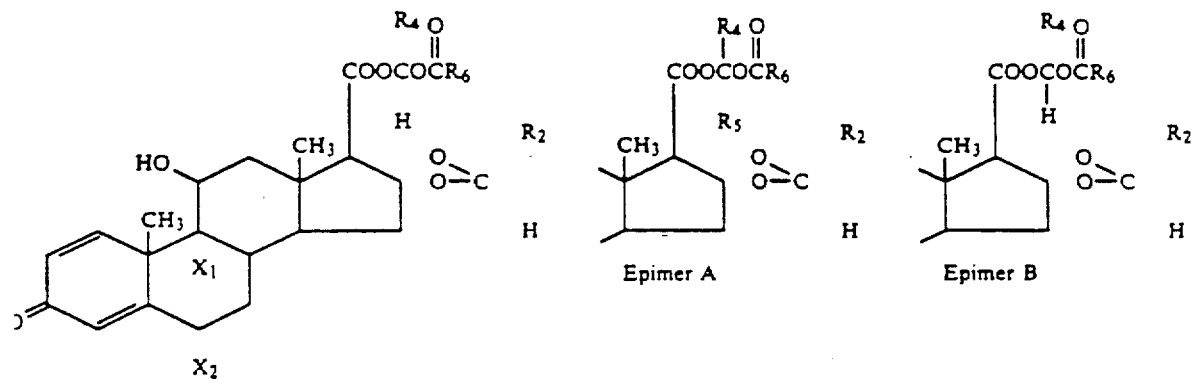

should read --

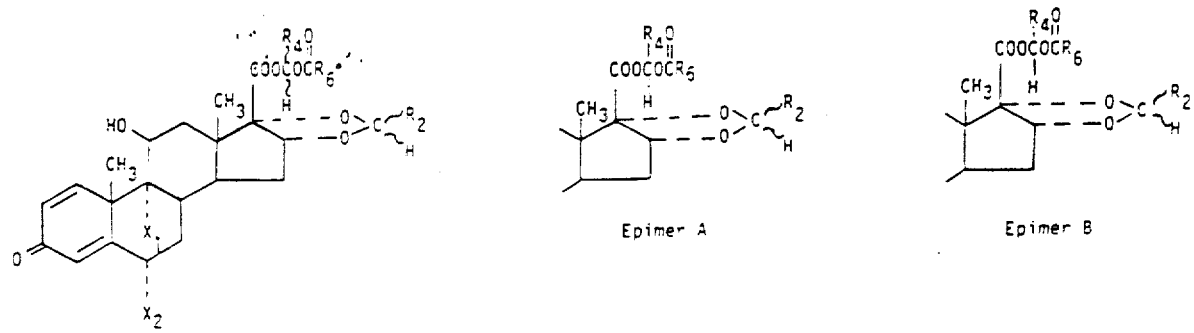

--;

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

Col. 17 and Col. 18, Table 3,

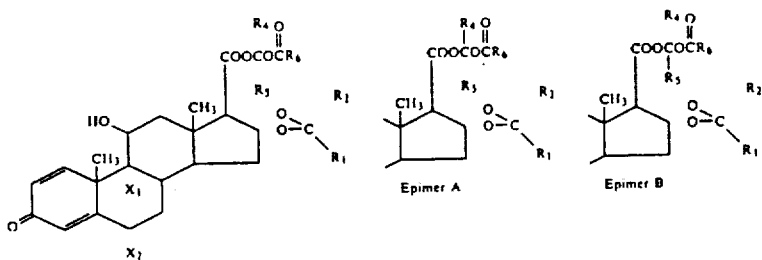

should read --

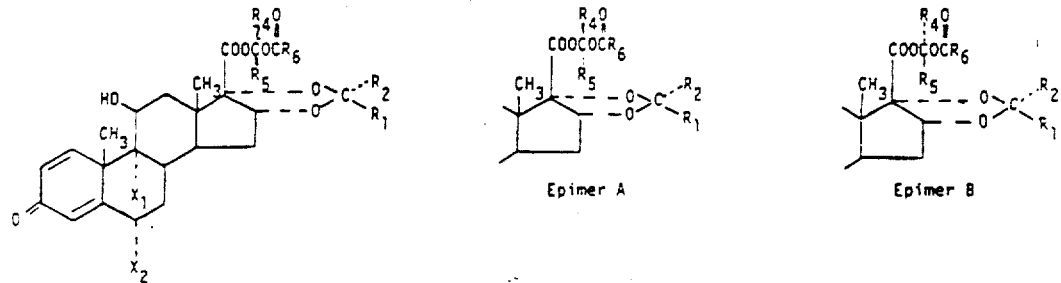

--

UNITED STATES PATENT AND TRADEMARK OFFICE
CERTIFICATE OF CORRECTION

PATENT NO. : 4,950,659

DATED : August 21, 1990

INVENTOR(S) : Paul H. Andersson, et al.

It is certified that error appears in the above-identified patent and that said Letters Patent is hereby corrected as shown below:

Col. 19 and Col. 20, Table 3 (con't),

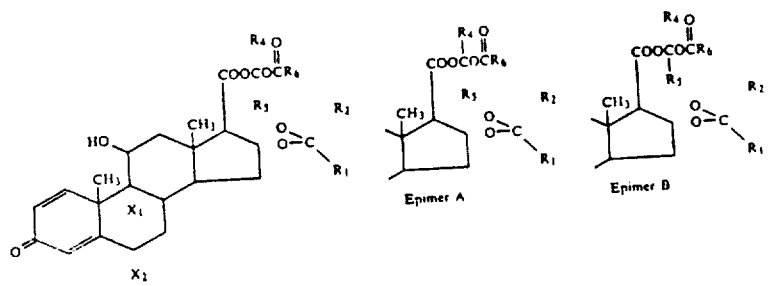

should read --

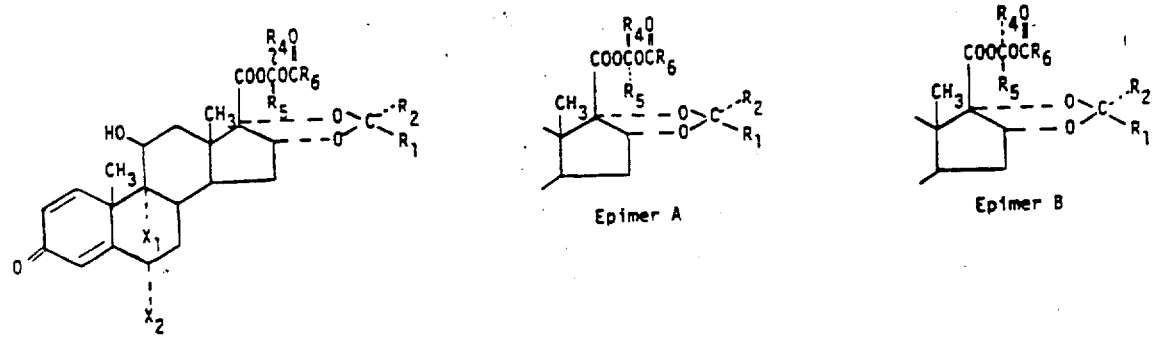

--;

UNITED STATES PATENT AND TRADEMARK OFFICE
CERTIFICATE OF CORRECTION

Page 15 of 15

PATENT NO. : 4,950,659
DATED : August 21, 1990
INVENTOR(S) : Paul H. Andersson, et al.

It is certified that error appears in the above-identified patent and that said Letters Patent is hereby corrected as shown below:

Col. 23, line 54 (claim 1)

$$-(CH_2)_m-\widehat{CH(CH_2)}_n$$

should read -- $-(CH_2)_m-\widehat{CH(CH_2)}_n$ --;

Signed and Sealed this

First Day of September, 1992

Attest:

DOUGLAS B. COMER

Attesting Officer

Acting Commissioner of Patents and Trademarks